US006959216B2

(12) United States Patent
Faghri (10) Patent No.: US 6,959,216 B2
(45) Date of Patent: Oct. 25, 2005

(54) ELECTRONIC MUSCLE PUMP (75) Inventor: Pouran D. Faghri, Mansfield, CT (US)

(73) Assignee: University of Connecticut, Farmington, CT (US)

(*) Notice: Subject to any disclaimer, the term of this patent is extended or adjusted under 35 U.S.C. 154(b) by 432 days.

(21) Appl. No.: 10/233,191

(22) Filed: Aug. 30, 2002

(65) Prior Publication Data
US 2003/0060740 A1 Mar. 27, 2003

Related U.S. Application Data (60) Provisional application No. 60/325,482, filed on Sep. 27, 2001.

(51) Int. Cl.[7] .............................................. A61N 1/36
(52) U.S. Cl. ...................................................... 607/48
(58) Field of Search .................................. 607/48–72

(56) References Cited

U.S. PATENT DOCUMENTS

| 3,773,051 A | * | 11/1973 | Holcomb et al. | ............. | 607/61 |
| 4,177,819 A | * | 12/1979 | Kofsky et al. | ................. | 607/63 |
| 4,569,352 A | * | 2/1986 | Petrofsky et al. | ............. | 607/49 |
| 4,658,830 A | | 4/1987 | Sarnoff | ........................ | 128/696 |
| 5,107,835 A | | 4/1992 | Thomas | ................... | 128/419 R |
| 5,109,846 A | | 5/1992 | Thomas | ....................... | 128/421 |
| 5,358,513 A | | 10/1994 | Powell, III et al. | ........... | 607/48 |
| 5,396,896 A | | 3/1995 | Tumey et al. | ................ | 128/690 |
| 5,556,422 A | | 9/1996 | Powell, III et al. | ........... | 607/48 |
| 5,662,693 A | | 9/1997 | Johnson et al. | ................ | 607/49 |
| 5,674,262 A | | 10/1997 | Tumey | ......................... | 607/48 |
| 5,725,563 A | | 3/1998 | Klotz | ........................... | 607/62 |
| 5,782,893 A | | 7/1998 | Dennis, III | ................... | 607/48 |
| 6,213,933 B1 | | 4/2001 | Lin | ............................. | 600/13 |

OTHER PUBLICATIONS

"Venous Hemodynamics of the Lower Extremities in Response to Electrical Stimulation" by Pouran D. Faghri, MD, John J. Votto, DO, Christopher F. Hovorka, BS; Arch Phys. Med. Rehabil. vol. 79, Jul. 1998.

"A Comparison of Three Mechanical Interventions in Reducing Lower Limb Edema in Stroke Patients" by Pouran D. Faghri, MD, MS, Christopher F. Hovorka, BS, and William J. Pesce, DO, University of Connecticut, Dept. of Health Promotion & Allied Health Sciences, Storrs, CT, and Hospital for Special Care, New Britain, CT; RESNA '98—Jun. 26-30, 1998.

"Central Hemodynamic Responses to Loaded and Unloaded ES-Induced and Voluntary Contractions of the Lower Leg" by P.D. Faghri, J.D. Votto, and C.F. Hovorka, Dept. of Health Promotion & Allied Health Sciences, School of Allied Health, University of Connecticut, and Hosp. For Special Care, New Britain, CT; Neural Prosthesis: Motor Systems 5 (NP '97).

(Continued)

Primary Examiner—Scott M. Getzow
(74) Attorney, Agent, or Firm—McCarter & English LLP (57) ABSTRACT An electronic muscle pump includes an ankle position sensor which provides an initiation signal when a patient's foot is mal-positioned relative to the leg. A controller has a sequencer and an exercise mode selector switch. The exercise mode selector switch closes a signal path between the ankle position sensor and the sequencer in the off position and opens the signal path in the on position. The sequencer is switched from an off condition to an on condition when the initiation signal is received for a predetermined period of time and is repetitively switched between the on and off conditions a predetermined number of times when the exercise mode selector switch is in the on position. A functional electrical stimulator provides a stimulation current to one or more muscles, via electrodes, when the sequencer is in the on condition.

19 Claims, 5 Drawing Sheets

OTHER PUBLICATIONS

"Circulatory Responses to Elecrical (sic) Stimulation of Lower Limb Muscles of Healthy Subjects" by Pouran D. Faghri, MD, MSc, John Votto, MD, University of Connecticut & Hospital for Special Care, New Britain, CT, RESNA '97—Jun. 20-24, 1997.

"Venous Hemodynamic Response to Electrical Stimulation" by Faghri PD, Votto JJ, Hovorka CF; Arch Pys. Med. Rehabil. 1998: 79: 842-8.

"Evaluation of Mechanical Methods for Prevention of Deep Venous Thrombosis" by Pouran D. Faghri, MD; University of Connecticut; From the Field—Clinical Kinesiology, vol. 52, No. 1, Spring, 1998.

"Electrical Stimulation—Induced Contraction to Reduce Blood Stasis During Arthroplasty" by Pouran D. Faghri, Hjalmar F. Pompe Van Meerdervort, Roger M. Glaser, and Stephen F. Figoni; IEEE Transactions on Rehabilitation Engineering, vol. 5, No. 1, Mar. 1997.

* cited by examiner

ELECTRONIC MUSCLE PUMP

CROSS-REFERENCE TO RELATED APPLICATIONS

This application claims the benefit under 35 U.S.C. §119(e) of U.S. Provisional Patent Application Ser. No. 60/325,482, filed Sep. 27, 2001.

BACKGROUND OF THE INVENTION

This invention relates generally to medical apparatus for improving venous blood flow from the lower leg. More particularly, the present invention relates to medical apparatus for stimulating the calf muscle pump function.

It is generally assumed that the deep venous system carries 90% of the blood from the lower limb. Transition from rest to normal rhythmic exercise such as walking, is accompanied by dramatic changes in the pressure and the flow in the veins of the lower limb. When a subject moves from a supine to a standing position, the foot venous pressure rises from 15 to around 115 mm Hg because of the hydrostatic pressure. Fifteen to 20% of the total blood volume may pool in the lower extremities and 10% of plasma volume is lost to tissues after 20 to 30 minutes of passive standing. During this time the hydrostatic pressure within the blood vessels of the lower extremities increases leading to an increased transcapillary filtration into the interstitial space. Concomitantly, the re-absorption of interstitial fluid is reduced, resulting in an increased extravascular fluid volume and edema. The longer the blood stagnates in the lower limb the higher the incidence of secondary conditions such as venous insufficiency (varicose vein), blood clot formation in the lower leg (known as deep venous thrombosis or DVT). The clot forming in the leg will be eventually released into the circulating blood and may cause a life threatening condition known as pulmonary embolism (PE).

Any condition that predisposes a person to a stationary position without the opportunity for activation of the physiologic muscle pump will increase that person's chance for the development of venous insufficiency and subsequent DVT, edema and PE. The followings are some of the examples that predispose a person to the development of DVT and PE:

1 Occupations and work posture that may require a person to sit or stand for a long period of time (i.e.: computer programmers, pilots).
2 Airplane passengers during long distance flight in the economy section (this is known as Coach Syndrome or Economy Class Syndrome).
3 Astronauts during weightlessness (zero gravity), which increase the pooling of the blood to the lower limb due to the negative pressure.
4 Patients during prolonged surgery and during anesthesia as well as during recovery.
5 Elderly due to inactivity, chronic disease and wheel chair confinement, and chronic vascular disorders.
6 Finally those with muscle paralysis (i.e.: spinal cord injured, stroke patients and those with multiple sclerosis), which are unable to contract the lower limb muscles due to paralysis.

In these situations where voluntary calf muscle pump function is not attainable (situational space limitation for movement, i.e.: airplane passengers or occupations), as well as conditions where voluntary muscle activation is not possible due to paralysis (i.e.: spinal cord injury, stroke) another means of activation is required.

Elastic stockings provide a modest benefit in augmenting superficial venous flow velocity. However, they are not effective in improving deep veins flow and have no effect on venous sinuses (where, the clot forms). Such stockings require meticulous care and must be changed routinely.

Intermittent calf compression has been extensively investigated for the prevention of postoperative venous thrombosis. Pressure is applied to the calf by intermittent inflation of a cuff or boot. The external pressure is applied to the calves over the peripheral veins (40 torrs was most often used), followed by a longer period of deflation and then an interval to allow refilling of the veins before recycling every 1–2 minutes., The external pneumatic devices are not portable due to their large body and need an external electrical outlet. Therefore, they are more useful in the operating room and in recovery where patients have limited ambulation. Many of the pneumatic devices in current use are uncomfortable because they produce excessive sweating beneath the plastic sleeves. They cannot be worn while the patient is ambulatory. They are bulky, require a connection to air compressor, and are associated with compartment syndrome.

The action of the calf muscle pump has an important effect in reducing the venous pressure. The normal functioning of the calf muscle pump (also called venous pump of the calf) is defined as the ability to keep the venous outflow from the lower leg equal to the arterial inflow during exercise, without undue dilation of the veins of the lower leg. The muscular pumping mechanism has important functional connotations: it drastically lowers the venous and capillary pressures, reduces the blood volume contained within the veins of the leg. The veins also act as a reservoir that releases stored blood during muscular contractions; momentarily accelerating the return of venous blood from the leg to the central circulations, therefore increasing exercise capability. The muscle pump also prevents the development of edema in the lower extremities by promoting lymph flow in an upright posture.

Functional electrical stimulation (FES) has been used to induce purposeful movements in the paralyzed muscles in the person with spinal cord injury and strokes patients. The basic idea behind FES is to use electrical current at the level appropriate for an individual to induce function in the paralyzed skeletal muscles. Most of the studies have used FES to induce function in the paralyzed muscle of people with spinal cord injury or stroke to cause contraction for the purpose of exercise.

It should be noted that about 90% of the circulating blood is carried through venous system, this system basically acts as reservoirs to release stored blood in its sinusoidal deep veins during muscle contractions, momentarily accelerating the return of venous blood, preventing blood stasis and also preventing edema by promoting lymph flow. Contraction of the calf muscle powerfully compresses the veins, with one-way valves which prevent back flow, and propels the blood to the heart via the venous system. During relaxation, the pressure in the veins drops sharply and refilling results from small capillaries. This mechanism increases pre-load on the heart via the Frank-Starling mechanism. The Frank-Starling mechanism states that an increase in venous return results in a greater enddiastolic volume and within a few beats blood flow out of the heart will equal flow into the heart. The skeletal muscle pump has been referred to as the peripheral venous heart. Therefore activation of the these muscles by FES specially in those who are confined to wheelchair (i.e.: people with paralysis and elderly) will actually improve the circulation of the blood and make more blood available for every day activities, specially wheel chair propulsion and eventually leads to a better quality of life.

Pneumatic venous foot pumps applied to the foot are systems designed to stimulate the venous foot pump artificially by flattening of the plantar arch. The device has been shown to maintain venous circulation as effectively as does normal walking. These systems are also not practical due to power requirements and limitation of movement during their use.

Studies have shown that the soleus muscle and its veins act as a peripheral pump, filling during relaxation and emptying during contraction. Functional neuromuscular electrical stimulation (FES) of the calf musculature duplicates the effects of this pumping mechanism during ambulation and effectively empties the venous blood and improve the blood flow. When analyzing the characteristics of blood flow following FES application in comparison with venous foot pump, it has been shown that venous foot pump caused a steady rise in the velocity of blood in the vein which slowly returned to baseline over a period of two to three seconds. Calf stimulation, however, produced nearly an instantaneous rise in the velocity of the blood flow in the veins, which then fell to zero. The fall to zero of the blood flow in the lower legs of subjects after calf stimulation suggested that it was quickly emptying the vessels on which it was acting and no more flow resulted. The net zero flow could be due to refilling from distal and proximal veins. This fall to zero of blood flow was not seen when the venous foot pump was utilized suggesting that blood is being pushed past the orifices of the sinuses allowing blood to remain stagnant within the sinuses. Analyzing the velocity spectra, the venous foot pumps caused laminar flow within the veins while the calf stimulation caused turbulent. Therefore, calf muscle stimulation is more effective than the venous foot pump because it provided greater peak velocity after stimulation and the appearance of complete purging of the blood from the veins of the lower extremity to the heart.

SUMMARY OF THE INVENTION

Briefly stated, the invention in a preferred form is an electronic muscle pump which includes a controller having a sequencer and an exercise mode selector switch. The exercise mode selector switch closes a signal path between the ankle position sensor and the sequencer in the off position and opens the signal path in the on position. The sequencer is switched from an off condition to an on condition when the initiation signal is received for a predetermined period of time and is repetitively switched between the on and off conditions a predetermined number of times when the exercise mode selector switch is in the on position. A functional electrical stimulator provides a stimulation current to one or more muscles, via electrodes, when the sequencer is in the on condition.

The electronic muscle pump also includes an ankle position sensor which provides the initiation signal to the sequencer when a patient's foot is mal-positioned relative to the leg. The controller also has an ankle position threshold generator providing a reference signal and a comparator in electrical communication with the ankle position threshold generator and the ankle position sensor. The comparator compares the position signal to the reference signal and sends the initiation signal to the sequencer when the position signal and the reference signal are in a predetermined relationship.

The ankle position sensor includes a linear potentiometer having a housing which is mounted to a patient's leg and a potentiometer shaft which is connected to the foot extending from the leg. Relative movement between the foot and the leg changes the electrical resistance of the potentiometer providing a voltage signal which is indicative of the relative position. The ankle position sensor also includes a sensing wire and a tension take-up spring. The distal end of the sensing wire is mounted to the patient's foot. One end of the tension take-up spring is mounted to the proximal end of the sensing wire and the other end is mounted to the distal end of the potentiometer shaft. The tension take-up spring absorbs any tension resulting from relative movement between the patient's foot and leg which would urge the potentiometer shaft beyond a mechanical limit of motion. A return spring connected to the proximal end of the potentiometer shaft biases the potentiometer shaft to its original position.

The controller further includes an exercise mode selector switch which may be switched between on and off positions. The exercise mode selector switch enables the ankle position sensor in the off position, allowing the initiation signal to pass through to the sequencer. The exercise mode selector switch disables the ankle position sensor in the on position, blocking the initiation signal, but causes the sequencer to repetitively switch between the on and off conditions a predetermined number of times. The controller further includes a counter for counting the number of switches between the on and off conditions.

The objects and advantages of the invention will become apparent from the drawings and specification.

BRIEF DESCRIPTION OF THE DRAWINGS

The present invention may be better understood and its numerous objects and advantages will become apparent to those skilled in the art by reference to the accompanying drawings in which.

DETAILED DESCRIPTION OF THE PREFERRED EMBODIMENT

With reference to the drawings wherein like numerals represent like parts throughout the several figures, an electronic muscle pump (EMP) in accordance with the present invention is generally designated by the numeral 10.

The EMP 10 includes a position sensor 12, a controller 14, and a two to four-channel electrical stimulator 16 (with surface electrodes 18). The system preferably incorporates up to four channels for additional muscles to be stimulated. During use, it indicates (via an audible signal 20) when there is no movement in the ankle joint to activate the muscle pump, which could lead to stagnation of the blood in the lower limb and subsequent DVT. This audio biofeedback 22 enables the person first to voluntarily correct the position within 5 seconds by doing a plantar flexion/extension. If the person does not respond appropriately, the electrical stimulator is automatically activated to induce contractions of the gastronomies and tibialis anterior muscles (e.g., 12 seconds ON-OFF for 5 cycles) to induce plantar flexion (like tip toe exercise) in order to activate the muscle pump. The EMP 10 can also be used in an exercise mode 24, which will cause activation of the involved muscles according to a daily schedule to prevent marked deterioration of the muscles and to facilitate blood flow circulation in the lower limb. This function is especially important for people with lower limb muscle paralysis such as spinal cord injury, stroke, or other upper motor neuron lesions that are not able to correct the position by appropriate muscle contraction through biofeedback.

The system could be mounted in a wheel chair and programmed to induce rhythmic lower limb muscle activation during wheel chair propulsion. This will provide more blood to the central circulation and the upper limb muscles and therefore, better exercise capability or wheelchair propulsion ability and subsequently better quality of life. Please note that in biofeedback mode 22, the user still has a choice of allowing the electrical stimulation to kick in. The warning buzzer 20 would allow the person to position himself or herself and be ready for the stimulation.

EMP 10 is a small, lightweight, portable device that could be continuously worn by person during activities of daily living. It warns the person of hazardous postural position that can lead to clot formation or DVT. It can train (via biofeedback) the person to be more aware of their vulnerable posture and allow them to correct it if they are able-bodied due to it's biofeedback capability. Furthermore, it can exercise/train the muscles via preset protocols when put in exercise mode to improve function and circulations.

Figure 1:
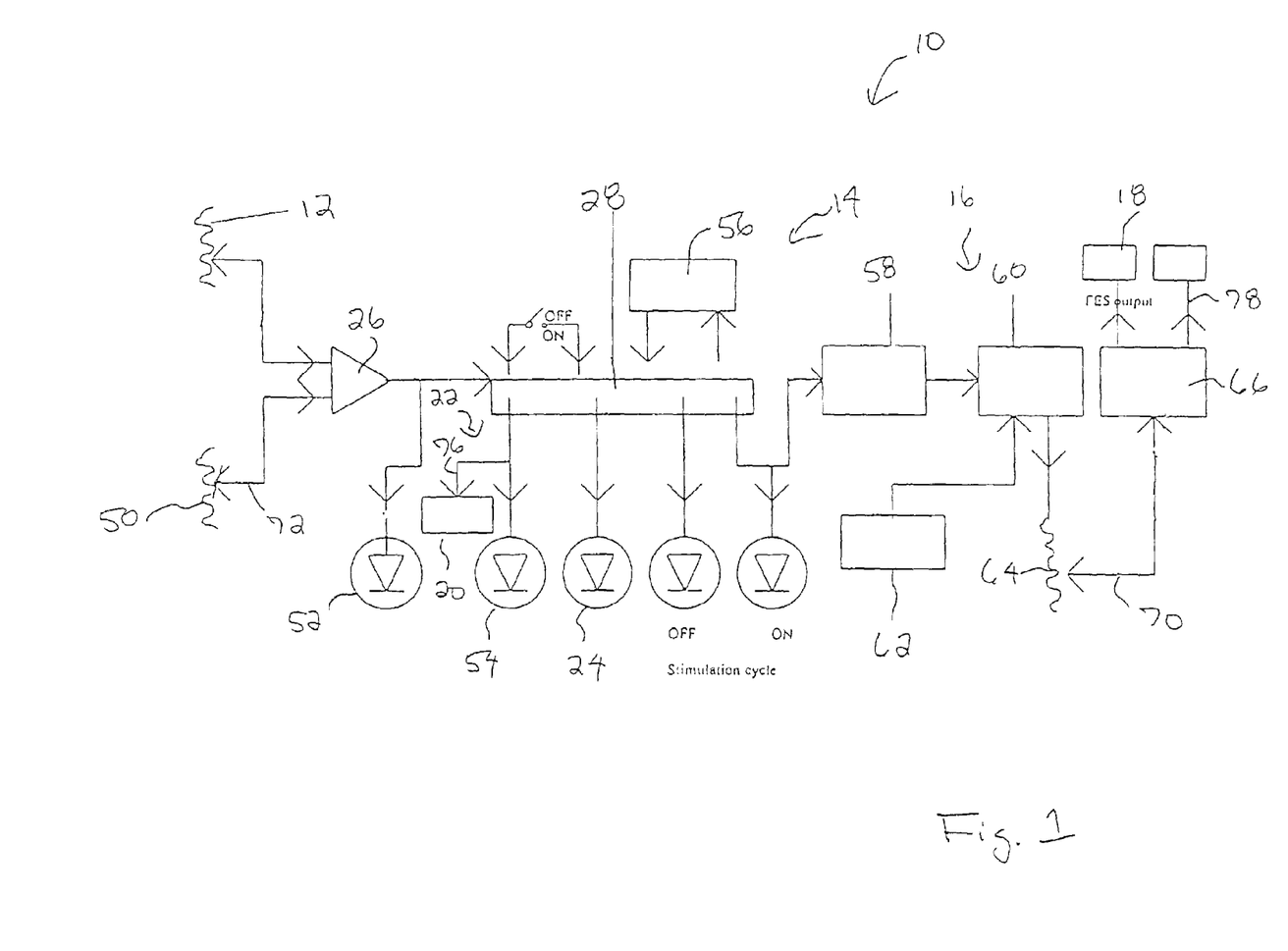
FIG. 1 is a functional block diagram of an electronic muscle pump in accordance with the invention.

The circuitry for the EMP 10 includes an ankle position sensor 12, a controller 14 having a comparator 26 and a sequencer 28, and a functional electrical stimulator 16. FIG. 1 provides a block diagram of the EMP 10, whereas FIG. 2 provides the waveforms at each stage of the circuitry. The following describes the operation of each stage of the EMP 10 during patient use.

Figure 3:
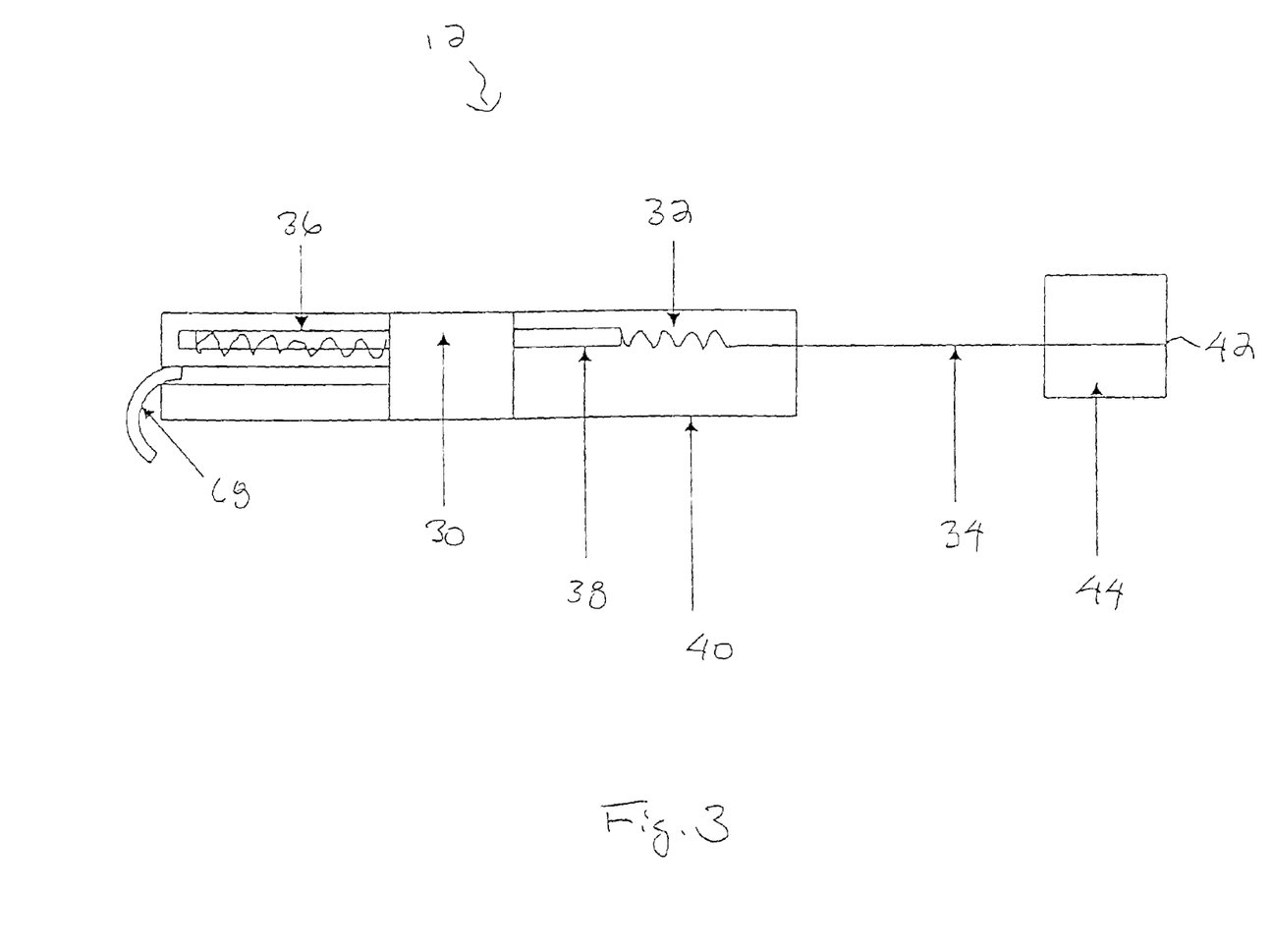
FIG. 3 is schematic diagram of the position sensor of FIG. 1.

The ankle position sensor 12, diagramed in FIG. 3 is essentially a linear potentiometer 30 coupled through a tension take-up spring 32 to a length of flexible wire 34. A return spring 36 is used to ensure that the potentiometer shaft 38 returns to the initial position when tension is not applied to the wire 34 (i.e., the ankle in 90° flexion). The sensor 12 could be mounted into a garment such as long stockings in a vertical position with the back edge of the housing 40 positioned over the patella as a landmark. The free end 42 of the wire 34 is secured by tape 44 or the like over the dorsal surface of the foot 46. When the ankle moves in plantar flexions the distance from where the potentiometer 30 is secured to where the wire 34 is secured increases. This results in a pulling on the wire 34, which, in turn, pulls the shaft 38 of the linear potentiometer 30, increasing its electrical resistance and the voltage that is dropped across the linear potentiometer 30. If the linear potentiometer 30 is at its mechanical limit of motion, the tension take-up spring 32 absorbs any extra tension that may result from extreme movement of the foot 46 to protect the potentiometer 30 from damage. When the foot 46 is repositioned to it's original position (90° flexion), the return spring 36 pulls the potentiometer shaft 38 back to its initial position.

The comparator 26 works in conjunction with the ankle position sensor 12, and is adjusted to determine when the involved leg 48 is in a hazardous position which can lead to pooling of the blood. This is done by configuring the linear potentiometer 30 in the sensor 12 as a voltage divider so that it provides a voltage that is disproportional to the amount of the ankle flexion. This "position voltage" is compared to a reference voltage that is individually set by the foot/ankle position threshold potentiometer 50 (on the front panel). This controls the range of foot/ankle movement that will be permitted for the EMP 10 to be activated. When the ankle does not move in plantar flexions, the "position voltage" is less than the reference voltage and the output of the comparator 26 goes low, indicating that the muscle pump is not activated. This signal activates an LED 52 on the front panel and also causes the sequencer to take action.

The sequencer 28 controls the action of the EMP 10 upon detection of inappropriate ankle position. When the sequencer 28 receives a low signal from the comparator 26, it activates a timer 54 for a 5 second period. This produces a "wait time" where a warning buzzer/vibration 20 and an LED 52 on the front panel are turned on. The auditory feedback signal 20 alerts the patient to the ankle position problem and allow a 5 second time for voluntary correction of the position. The patient could perform plantar flexion exercises 5 times voluntarily or allow the EMP 10 to do the simulation. During this "wait time", if the patient corrects the position by dorsi flexion or extension (causing the output of the comparator 26 to go high), the timer 54 is reset and the device goes back into the standby mode. If, however, the ankle position is not corrected in this time, the sequencer 28 then operates the functional electrical stimulator 16 for 5 cycles of 12 seconds ON and 12 seconds OFF to contract the lower leg muscles in a repetitive fashion. Regardless of the position of the ankle, the sequencer 28 will remain in this mode until the 5 cycles of electrical stimulation are completed. The counter circuit 56 keeps track of the number of stimulation cycles. Afterwards, the system goes to the standby mode for 5 minutes during which no action will take place. After 5 minutes if the ankle is again mal-positioned, the sequencer 28 will repeat the "wait time" of 5 seconds (with active warning buzzer 20), followed by a repetition of 5, which is then detected by the EMP 10. If the linear potentiometer 30 is at its mechanical limit of motion, the tension take-up spring 32 absorbs any extra tension that may result from extreme stretching to protect the potentiometer 30 from damage. (Note that the operating protocol and time durations are adjustable to obtain optimal results.) Details of the sequencer operation are provided by the logic flow diagram in FIG. 1.

Figure 2A:
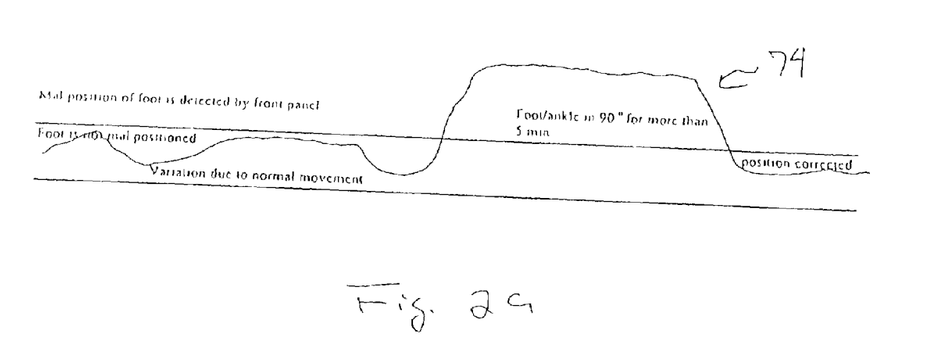
FIGS. 2a to 2g illustrate the waveforms of electrical signals within the electronic muscle pump of FIG. 1.
Figure 2B:
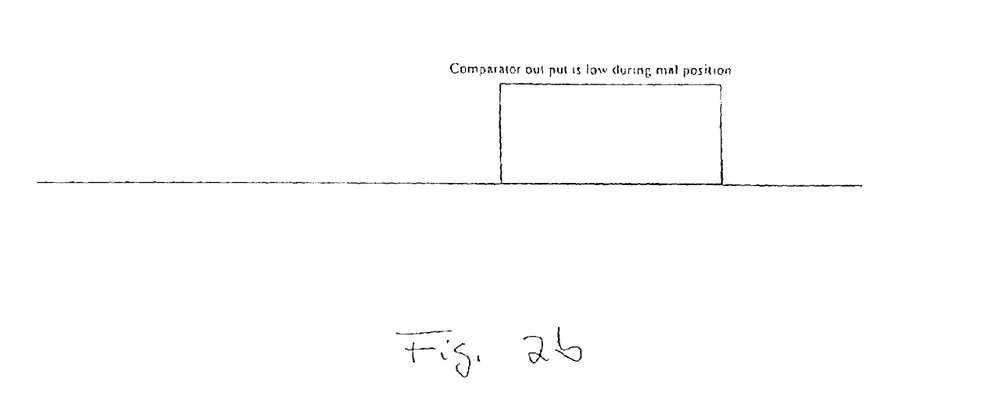
Figure 2C:
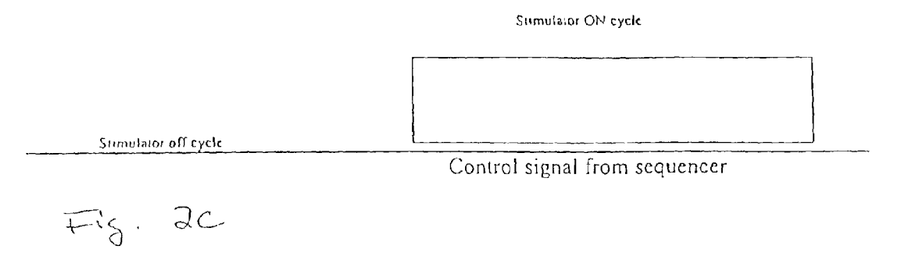
Figure 2D:
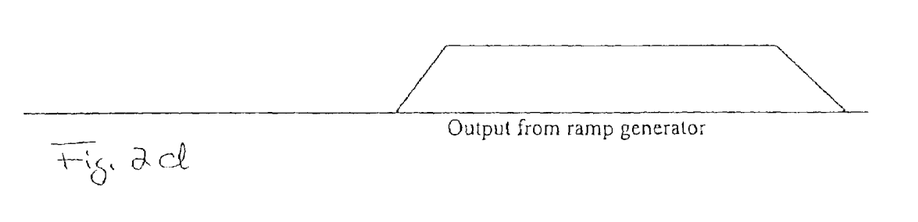
Figure 2E:
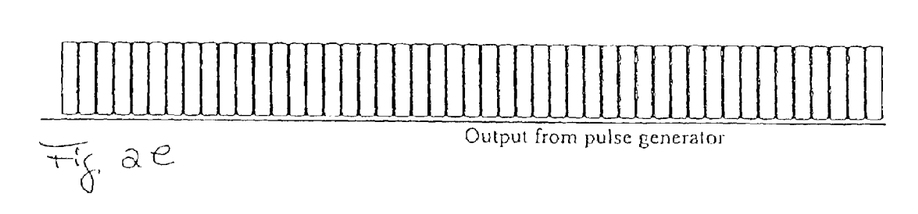

The functional electrical stimulator 16 causes contraction of the lower limb muscles (Gastronomies and tibialis and if necessary sequential contraction of quadriceps and hamstrings) when enabled to do so by the sequencer 28. The sequencer signal is simply ON (comparator output goes low) or OFF (comparator output goes high) (FIG. 2c). When the sequencer is ON, the ramp generator 58 outputs a voltage that ramps linearly from zero to the operating level in 12 second. When the sequencer is OFF, the ramp generator 58 then ramps from the operating level back to zero in 12 seconds (FIG. 2d). This results in a gradual application and removal of stimulation, thereby avoiding sudden, jerky contractions that may damage the joint. Note that when the sequencer 28 goes OFF, the output from the ramp generator 58 does not immediately go low, but simply starts ramping to zero at this time.

Figure 2F:
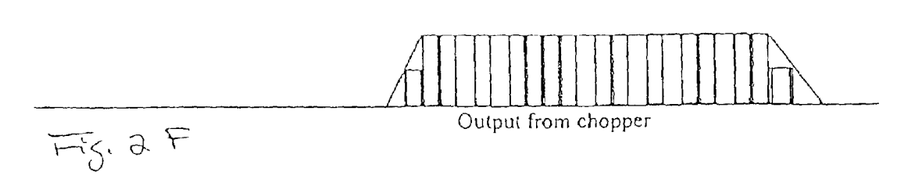
Figure 2G:
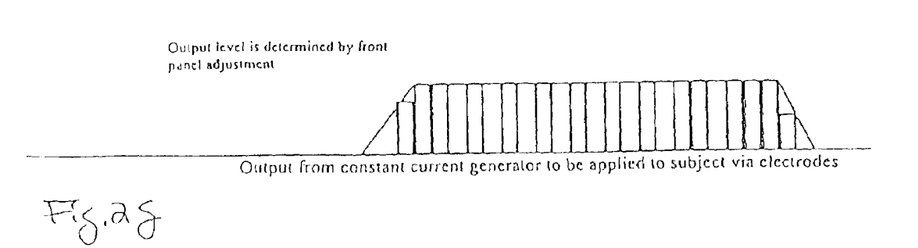

The DC voltage output from the ramp generator 58 is fed into the chopper 60 (driven by the pulse generator 62, (FIG. 2e) which chops the signal into narrow pulses of a frequency (35 Hz) and pulse width (300 $\mu$sec) determined by the pulse generator 62, but with the amplitude determined by the ramp generator 58 (FIG. 2f). In this manner, voltage controlled pulses are obtained. This signal then goes to a front panel potentiometer or level control 64 to allow for setting of the desired contraction intensity level. The signal (FIG. 2g) from the level control 64 then goes to a constant current amplifier 66 which then applies a current to the patient's electrodes 18 that is disproportional to input voltage (high linear potentiometer voltage—no stimulation, low linear potentiometer voltage—high stimulation) from the level control 64. To allow for a development of the relatively high voltages required to sustain the relatively high currents (150 mA maximum) through the skinlelectrode impedances, a step up transformer is preferably used for the constant current amplifier 66. This enables the use of a safe and compact low voltage battery for power. Note that once the contraction level adjustment is set, the operating level of the stimulator 16 does not vary, the stimulator 16 is simply turned on or off by the sequencer 28.

The EMP 10 has an "exercise mode" 24 of operation. This mode 24 could be used by the patient to voluntarily turn the stimulation on and off whenever they desire. This mode 24 is specially useful for paralyzed individuals who can not voluntarily contract their muscles and activate their physiologic muscle pump through biofeedback option. The system could be programmed to be on the exercise mode 24 whenever the person turns the system on. It is possible in this mode to allow the muscles to work against some resistance (i.e., on the foot rest of the wheelchair) during the FES-induced contraction. This will increase the integrity of the atrophied muscles, especially in those with paralysis.

When the EMP 10 is placed in the "exercise mode" 24, the sequencer 28 alternately turns the stimulator 16 ON and OFF for a certain number of repetitions according to a preset protocol. In this mode, the output of the comparator 26 is not used, and the electrical stimulation pulse and cycle parameters can be set to the desired values. (Which may not be the same as used for the ankle mal-position detection/correction mode).

Figure 4:
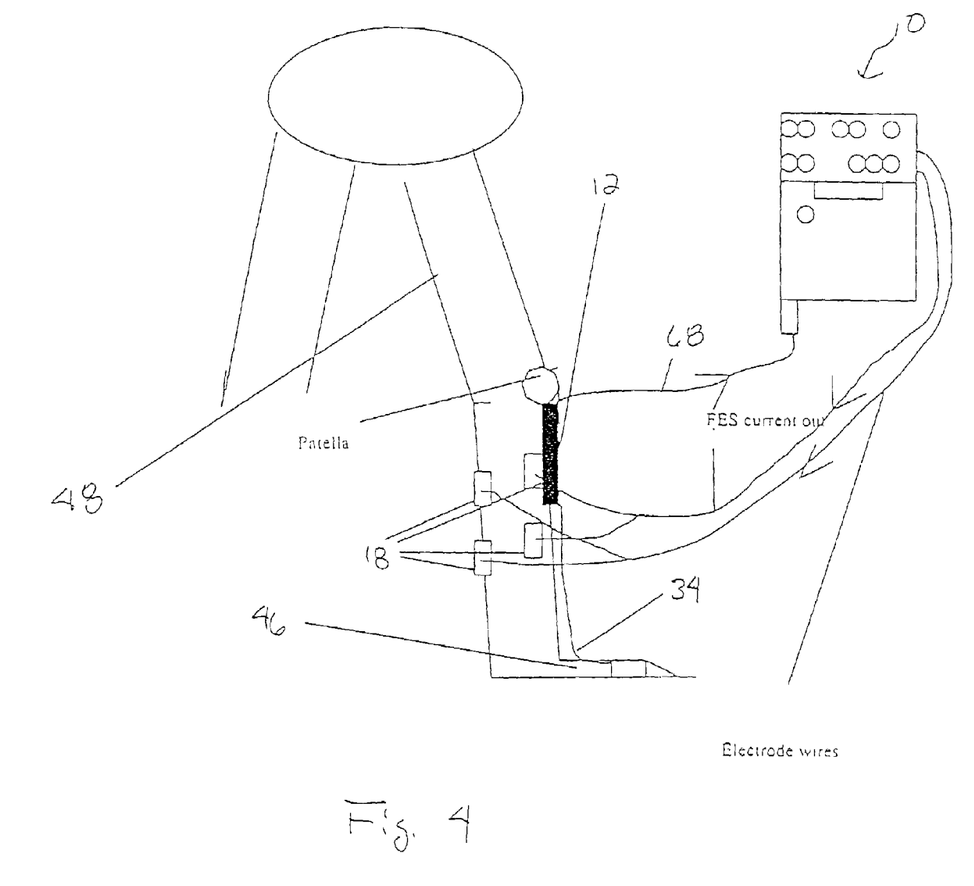
FIG. 4 is a schematic diagram showing the electronic muscle pump of FIG. 1 in use with a patient.

With reference to FIG. 4, the position sensor potentiometer 30 is applied to each leg 48 while the ankle is in either plantar flexion. The housing 40 of the sensor 12 (with the connecting cables 68 to the stimulator) is mounted inside a garment and is preferably secured with a velcro tape to the patella area as a landmark. The motion sensor wire 34 is securely taped 44 over the dorsal section of the foot 46, with all slack removed from the wire 34. The skin surface electrodes 18 are placed over the gastronomies and tibialis anterior (two electrodes per muscles). The electrical stimulation output current level for the gastronomies and tibialis anterior muscle is then set 70 for the desired action (ankle dorsiflexion followed be extension). Please note that special garments are available that can house the potentiometer 30 and the surface electrodes 18 inside them. This way the patient will wear the custom made garments and start the stimulation immediately.

After connecting the EMP 10 to the patient and setting the footlankle position threshold adjustment 72 and the electrical stimulation output level 70, the system is in the standby mode and ready to detect ankle mal-position. If mal-position occurs 74 (FIG. 2a) (foot in flexed 90° position for at least 5 minutes) a warning buzzer/vibration 20 will sound 76 for 5 seconds 54 to notify the patient of mal-position of the foot (FIG. 4). At this time, if the patient corrects the position within 5 seconds, the buzzer 20 will stop and the system will return to the standby mode (the patient will be trained to do the contractions for at least five times). If the malposition is not corrected, the electrical stimulation 78 will induce contractions for periods of 12 seconds ON and 12 seconds OFF, and this, cycle will be repeated five times. After five contraction cycles, the system 10 will return to the standby mode for five minutes. After five minutes, the system 10 is ready to detect subsequent mal-position of foot/ankle. The same procedure will continue while the system is in this alert mode. In addition, this EMP 10 can also be used to exercise or train the involved muscles on a daily basis to prevent marked deterioration, improve their integrity and facilitate both arterial and venous blood flow. Thus, in this mode the EMP 10 can be used by hemiplegic patients, and spinal cord injured individuals all day during activities of daily living. The system 10 could be easily mounted to a wheelchair, a standing frame, or regular chair and the person can use it to improve his/her circulation and thus prevent the unpleasant consequence of compromised circulation such as orthostatic hypotension, early fatigue, and overall reduction of the activities.

This system 10 could be an important tool to be used by wheelchair athletes to improve their performance by increasing the amount of the blood available to the upper extremities. The system 10 could be used by any person who is wheelchair confined or immobile for a long period of time to maintain the integrity of their muscles while improving the blood circulation within those muscles. The system 10 could be utilized during the rehabilitation of people with disability especially during tilting or standing to prevent orthostatic hypotension and to prevent intolerance to standing and tilting by moving the venous blood into the central circulation. The system 10 could be integrated to the surgical beds to provide muscle-pumping function during surgery while under anesthesia as well as post surgery. The system 10 could be used by general population who have to stay in one position such as sitting or standing for a long period of time (i.e., compute programmers, airplane travelers) which predispose them to, blood stasis in the lower leg and subsequent clot formation and DVT. The system 10 could be used by astronauts who have significant pooling of the blood to their lower extremities due to negative pressure induced during out of space flights. The system 10 is very small (could be placed in the packet of a shirt), is portable, and could be operated by the person at any situation. The system 10 could be integrated into any devices such as sport wheelchair, regular wheelchair, chair, standing frames, surgical bed, etc. and could be timed for contraction with the push of a button.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An electronic muscle pump comprising:
   a controller including a sequencer switchable between an on condition and an off condition, the sequencer providing a low level output signal in the on condition and a high level output signal in the off condition;
   a functional electrical stimulator including
      a ramp generator in electrical communication with the sequencer, the ramp generator producing a direct current output voltage having a value which ramps linearly from a zero level to a predetermined operating level on receipt of the low level output signal from the sequencer and which ramps linearly from the operating level to the zero level on receipt of the high level output signal from the sequencer, a pulse generator providing a pulse signal, a chopper in electrical communication with the ramp generator and the pulse generator, the chopper chopping the direct current output voltage of the ramp generator into a plurality of output pulses defining a frequency, each of the output pulses having a pulse width and an amplitude, the frequency and pulse width being determined by the pulse signal from the pulse generator, the amplitude being equal to the level of the direct current output voltage, and a current generator in electrical communication with the chopper, the current generator providing a stimulation current having a magnitude variable between a zero stimulation value and a high stimulation value, the magnitude of the stimulation current being inverse to the amplitude of the output pulses;

an ankle position sensor in electrical communication with the sequencer, the ankle position sensor being adapted for providing a position signal proportional to the position of a foot relative to a leg and selectively switching the sequencer from the off condition to the on condition, and a plurality of electrodes adapted for transmitting the stimulation current to one or more muscles;

wherein the controller includes an ankle position threshold generator providing a reference signal and a comparator in electrical communication with the ankle position threshold generator and the ankle position sensor, the comparator comparing the position signal to the reference signal and sending an initiation signal to the sequencer when the position signal and the reference signal are in a predetermined relationship, wherein the ankle position sensor includes a linear potentiometer having a housing adapted for mounting to a patient's leg and a potentiometer shaft adapted for connection to the foot extending from the leg, whereby relative movement between the foot and the leg changes the electrical resistance of the potentiometer, and wherein the ankle position sensor includes a sensing wire and a tension take-up spring, the potentiometer shaft, the sensing wire, and the tension take-up spring each having oppositely disposed first and second ends, the first end of the sensing wire being adapted for mounting to the patient's foot, the first and second ends of the tension take-up spring being mounted to the second end of the sensing wire and the first end of the potentiometer shaft, respectively, and the tension take-up spring absorbing any tension resulting from relative movement between the patient's foot and leg which would urge the potentiometer shaft beyond a mechanical limit of motion.

2. The electronic muscle pump of claim 1 wherein the current generator includes a step up transformer.

3. The electronic muscle pump of claim 1 wherein the value of the output voltage of the ramp generator ramps linearly between the zero level and the operating level over a period substantially equal to twelve seconds.

4. The electronic muscle pump of claim 1 wherein the frequency is substantially equal to 35 Hz and the pulse width is substantially equal to 300 µsec.

5. The electronic muscle pump of claim 1 wherein the high stimulation value of the stimulation current is substantially equal to 150 mA.

6. The electronic muscle pump of claim 1 wherein the functional electrical stimulator further includes a potentiometer disposed intermediate the chopper and the current generator for varying the amplitude of the output pulses.

7. The electronic muscle pump of claim 1 wherein the controller further includes a counter for counting the number of switches between the on and off conditions.

8. The electronic muscle pump of claim 1 wherein the controller further includes an exercise mode selector switch selectively switchable between on and off positions, the exercise mode selector switch enabling the ankle position sensor in the off position and disabling the ankle position sensor in the on position, the sequencer repetitively switching between the on and off conditions a predetermined number of times when the exercise mode selector switch is in the on position.

9. An electronic muscle pump comprising:

an ankle position sensor adapted for providing an initiation signal when a patient's foot is mal-positioned relative to the leg;

a controller including
   a sequencer switchable between an on condition and an off condition, the sequencer being switched to the on condition on receiving the initiation signal from the ankle position sensor and
   an exercise mode selector switch selectively switchable between on and off positions, the exercise mode selector switch closing a signal path between the ankle position sensor and the sequencer in the off position and opening the signal path in the on position;

a functional electrical stimulator providing a stimulation current when the sequencer is in the on condition; and a plurality of electrodes adapted for transmitting the stimulation current to one or more muscles;

wherein the sequencer repetitively switches between the on and off conditions when the exercise mode selector switch is in the on position.

10. The electronic muscle pump of claim 9 wherein the ankle position sensor is in electrical communication with the sequencer, the ankle position sensor being adapted for providing the initiation signal which is proportional to the position of a foot relative to a leg and selectively switching the sequencer from the off condition to the on condition.

11. The electronic muscle pump of claim 10 wherein the controller further includes an ankle position threshold generator providing a reference signal and a comparator in electrical communication with the ankle position threshold generator and the ankle position sensor, the comparator comparing the position signal to the reference signal and sending an initiation signal to the sequencer when the position signal and the reference signal are in a predetermined relationship.

12. The electronic muscle pump of claim 11 wherein the ankle position sensor includes a linear potentiometer having a housing adapted for mounting to a patient's leg and a potentiometer shaft adapted for connection to the foot extending from the leg, whereby relative movement between the foot and the leg changes the electrical resistance of the potentiometer.

13. The electronic muscle pump of claim 12 wherein the ankle position sensor also includes a sensing wire and a tension take-up spring, the potentiometer shaft, the sensing wire, and the tension take-up spring each having oppositely disposed first and second ends, the first end of the sensing wire being adapted for mounting to the patient's foot, the first and second ends of the tension take-up spring being mounted to the second end of the sensing wire and the first end of the potentiometer shaft, respectively, the tension take-up spring absorbing any tension resulting from relative movement between the patient's foot and leg which would urge the potentiometer shaft beyond a mechanical limit of motion.

14. The electronic muscle pump of claim 13 wherein the ankle position sensor further includes a return spring connected to the second end of the potentiometer shaft.

15. The electronic muscle pump of claim 9 wherein the sequencer is switched to the on condition on receiving the initiation signal from the ankle position sensor for a predetermined period of time.

16. The electronic muscle pump of claim 9 wherein the sequencer repetitively switches between the on and off conditions a predetermined number of times when the exercise mode selector switch is in the on position.

17. The electronic muscle pump of claim 9 wherein the controller further includes a counter for counting the number of switches between the on and off conditions.

18. An electronic muscle pump comprising:
   a controller including a sequencer switchable between an on condition and an off condition, the sequencer providing a low level output signal in the on condition and a high level output signal in the off condition;
   a functional electrical stimulator including
      a ramp generator in electrical communication with the sequencer, the ramp generator producing a direct current output voltage having a value which ramps linearly from a zero level to a predetermined operating level on receipt of the low level output signal from the sequencer and which ramps linearly from the operating level to the zero level on receipt of the high level output signal from the sequencer,
      a pulse generator providing a pulse signal,
      a chopper in electrical communication with the ramp generator and the pulse generator, the chopper chopping the direct current output voltage of the ramp generator into a plurality of output pulses defining a frequency, each of the output pulses having a pulse width and an amplitude, the frequency and pulse width being determined by the pulse signal from the pulse generator, the amplitude being equal to the level of the direct current output voltage, and
      a current generator in electrical communication with the chopper, the current generator providing a stimulation current having a magnitude variable between a zero stimulation value and a high stimulation value, the magnitude of the stimulation current being inverse to the amplitude of the output pulses; and
   a plurality of electrodes adapted for transmitting the stimulation current to one or more muscles;
   wherein the ankle position sensor is in electrical communication with the sequencer, the ankle position sensor being adapted for providing a position signal proportional to the position of a foot relative to a leg and selectively switching the sequencer from the off condition to the on condition; and
   wherein the controller further includes an exercise mode selector switch selectively switchable between on and off positions, the exercise mode selector switch enabling the ankle position sensor in the off position and disabling the ankle position sensor in the on position, the sequencer repetitively switching between the on and off conditions a predetermined number of times when the exercise mode selector switch is in the on position.

19. The electronic muscle pump of claim 18 wherein the controller further includes a counter for counting the number of switches between the on and off conditions.

* * * * *